US008691252B2

(12) United States Patent
Savage

(10) Patent No.: US 8,691,252 B2
(45) Date of Patent: *Apr. 8, 2014

(54) STORAGE-STABLE, ANTI-MICROBIAL COMPOSITIONS INCLUDING CERAGENIN COMPOUNDS AND METHODS OF USE

(75) Inventor: Paul B. Savage, Mapleton, UT (US)

(73) Assignee: Brigham Young University, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,892

(22) Filed: Nov. 3, 2011

(65) Prior Publication Data

US 2012/0108561 A1    May 3, 2012

Related U.S. Application Data

(60) Provisional application No. 61/456,204, filed on Nov. 3, 2010.

(51) Int. Cl.
| | | |
|---|---|---|
| *A01P 1/00* | (2006.01) | |
| *A61K 31/56* | (2006.01) | |
| *A61K 31/568* | (2006.01) | |
| *A61K 31/57* | (2006.01) | |
| *A61K 31/573* | (2006.01) | |

(52) U.S. Cl.
USPC .............. 424/404; 514/169; 514/182; 422/28

(58) Field of Classification Search
None
See application file for complete search history.

(56) References Cited

U.S. PATENT DOCUMENTS

2005/0032765 A1*  2/2005  Savage et al. ................. 514/179
2007/0190558 A1*  8/2007  Savage et al. ..................... 435/6

FOREIGN PATENT DOCUMENTS

WO    WO 02/14342 A1    2/2002

OTHER PUBLICATIONS

Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999, pp. 1865-1868, XP004155984, ISSN: 0040-4039, DOI: 10.1016/S0040-4039(99)00075-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840, XP002528340, ISSN: 1523-7060, DOI: 10.1021/0L0062704.
Qunying Guan et al: "Supporting Information: Preparation and Characterization of Cholic Acid-Derived Antimicrobial Agents with Controlled Stabilities", Organic Letters, Aug. 17, 2000, pp. 1-7, XP55017313, Retrieved from the Internet: URL:http://pubs.acs.org/doi/suppl/10.1021/o10062704/suppl file/o10062704 sl.pdf.
PCT/US2011/059225, Jan. 31, 2012, International Search Report.

* cited by examiner

*Primary Examiner* — Brian Gulledge
*Assistant Examiner* — Michael P Cohen
(74) *Attorney, Agent, or Firm* — Workman Nydegger

(57) ABSTRACT

Storage-stable, anti-microbial compositions and products include a carrier and a ceragenin compound suspended in the carrier. Ceragenin compounds suspended in the carrier include a sterol backbone and a number of cationic groups attached to the sterol backbone via hydrolysable linkages. The carrier has a pH of 5.5 or less, which acts to stabilize the hydrolysable linkages and increase the shelf-life of the anti-microbial compositions and anti-microbial products. Nevertheless, the ceragenin compounds described herein are designed to break down relatively quickly (e.g., within about 5 days) if the pH environment of the ceragenin compounds is raised to about pH 6.5 or greater.

22 Claims, 5 Drawing Sheets

CSA-37

CSA-41

CSA-42

CSA-43

CSA-44

CSA-45

CSA-47

CSA-49

CSA-50

CSA-51

STORAGE-STABLE, ANTI-MICROBIAL COMPOSITIONS INCLUDING CERAGENIN COMPOUNDS AND METHODS OF USE

CROSS-REFERENCE TO RELATED APPLICATIONS

This application claims the benefit of and priority to U.S. Prov. Pat. App. Ser. No. 61/456,204 filed 3 Nov. 2010 and entitled "DIAPER WITH CSA ANTIMICROBIAL ACTIVE SITES," the entirety of which is incorporated herein by reference.

BACKGROUND

Eliminating and diminishing bacteria, viruses and other harmful microbes is a major concern. In a household or hospital setting, for example, bacteria and viruses may cause sicknesses such as a cold, flu or irritation or exasperation of allergies. Various products are available to reduce or eliminate bacteria, such as liquid or spray disinfectants. Liquid disinfectants are typically mixed with water and used to clean surfaces such as bathroom/kitchen counters, kitchen sink areas, food preparation areas, walls and baseboards, and the like. These liquid disinfectants and methods of surface cleaning may be effective in reducing microbial contamination.

For example, these liquid disinfectants may generally be effective in reducing microbial contamination by simple cleaning action or through the use of anti-microbials. However, many anti-microbial compounds are associated with the development of resistance, particularly among bacteria. In addition, many anti-microbials used in cleaning products are persistent environmental pollutants.

Food borne illnesses are also a major concern. Meats, poultry, and fish have long been known to be sources of food borne illnesses. Recently, cases of food borne illness transmitted by fruits and vegetables have also been reported. A number of liquid disinfectants are typically used in the food preparation industry. These typically employ dilute acids, oxidizing agents (e.g., dilute peracetic acid), and the like. However, the anti-microbial action of these compounds is particularly short in duration. Longer acting compounds that are capable of prolonging the shelf life of these fresh food (e.g., up to 5 days for fresh poultry) typically cannot be used either because they are potentially toxic to humans or because they may alter the taste or appearance of the foods that they are applied to.

BRIEF SUMMARY

Disclosed herein are storage-stable anti-microbial compositions, products incorporating these compositions, and methods for use of these compounds. The storage-stable, anti-microbial compositions include a ceragenin compound suspended in a carrier. The ceragenin compound includes a sterol backbone and a number of cationic groups attached to the sterol backbone via hydrolysable linkages. The hydrolysable linkages allow the compound to break down in the presence of water and/or a base.

The carrier has a pH of 5.5 or less, which acts to stabilize the hydrolysable linkages of the ceragenin compounds during storage. Upon use, the hydrolysable linkages break down relatively quickly (e.g., within about a week) when used in an environment that raises the pH (e.g., to a pH greater than 7).

Suitable examples of carriers include, but are not limited to, water, alcohols, oils, petroleum jelly, organic solvents, organic/aqueous emulsions, and combinations thereof. The hydrolysable linkages of the ceragenin compounds can be stabilized with any suitable compound that lowers the pH, such as an acid. In one example, the carrier may include water and an acid added in an amount sufficient to reduce the pH of the carrier to a pH of about 5.5 or less with the ceragenin compound suspended therein.

The ceragenin compounds may have a half-life greater than 2 months, 6 months, 1 year, or 2 years when suspended in the carrier. The stability typically increases with increasing pH. In one embodiment, the carrier has a pH less than 5, 4.5, 4, 3.5, or 3.

The ceragenin compound is also configured to break down when applied to a substrate in a particular environment. The ceragenin compound may include hydrolysable linkages that give the compound a half-life of less than 1, 5, 10, 20, or 40 days when the composition is applied to a substrate in an environment that raises the pH of the ceragenin compound to a pH greater than 6, 6.5, or 7. The increase in pH can occur from the ceragenin compound migrating into a more basic fluid (e.g., a fluid on the surface to be disinfected) or the pH can be raised by dilution of the carrier and/or dissolution of a basic molecule into the carrier.

Raising the pH of the environment in which the ceragenin compound is present allows the ceragenin to be storage-stable while being capable of effectively disinfecting a wide variety of surfaces and substances and then degrading to non-active compounds. The compositions can be used safely in large quantities without building up active ceragenins in the natural environment.

The compositions can be used as sprayable compositions (e.g., for use as a disinfectant in a spray bottle) or incorporated into gels or other products. The present invention also relates to methods for disinfecting a surface by applying the composition to the surface and allowing the pH environment of the ceragenin to change to cause hydrolysis of the cationic groups over a desired period of time.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Introduction

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

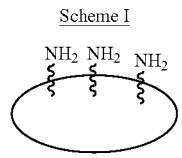

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

Figure 1:
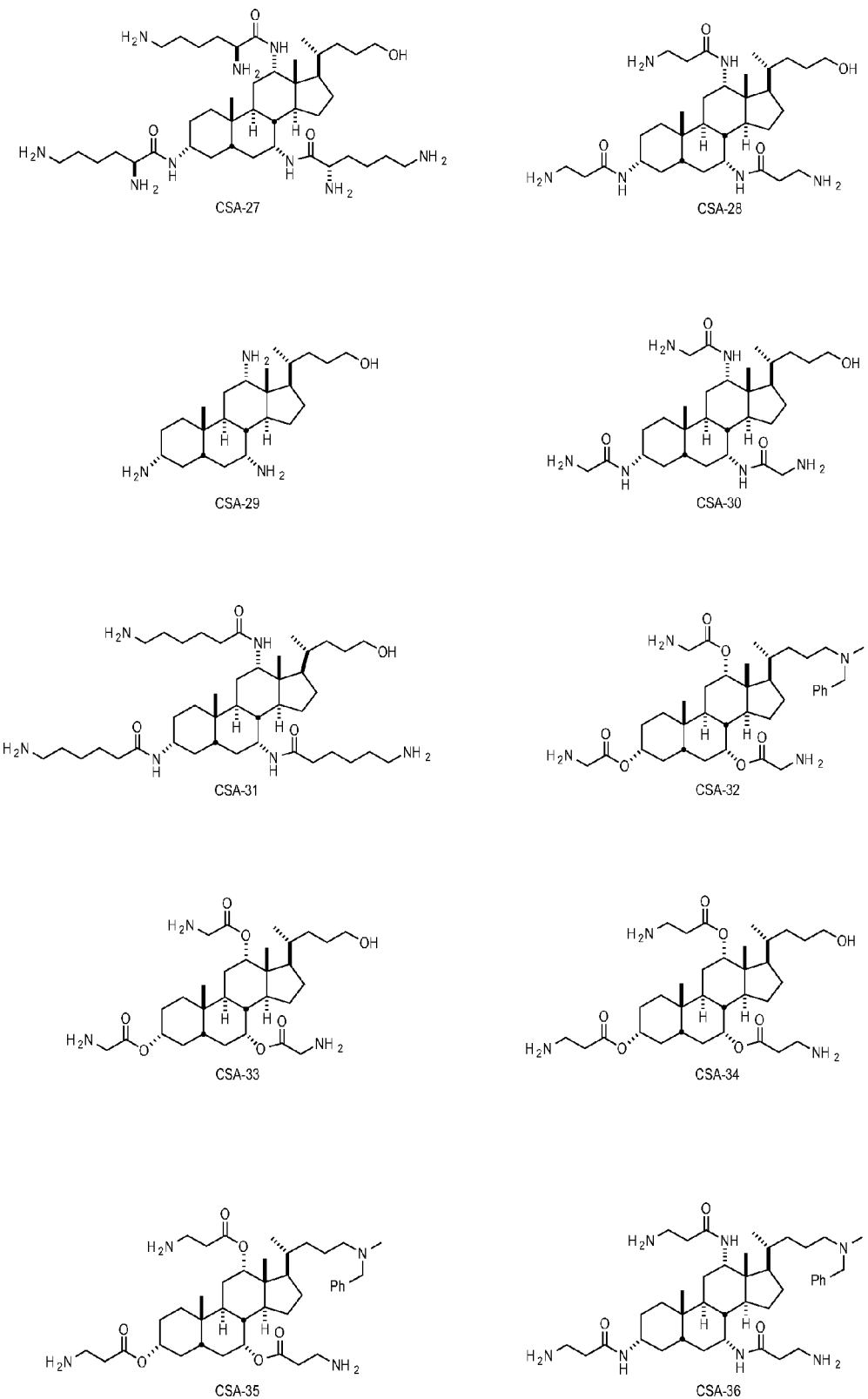
FIG. 1 illustrates exemplary cationic steroidal anti-microbial ("CSA") compounds.
Figure 1:
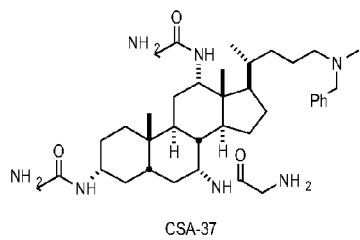
Figure 1:
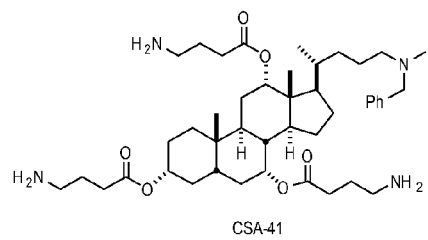
Figure 1:
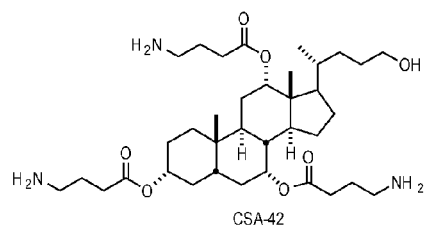
Figure 1:
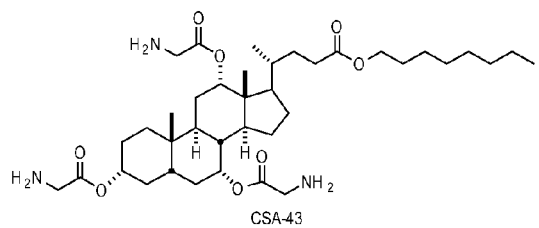
Figure 1:
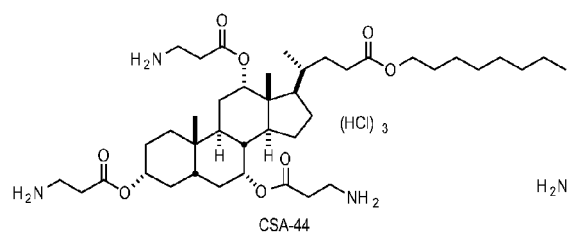
Figure 1:
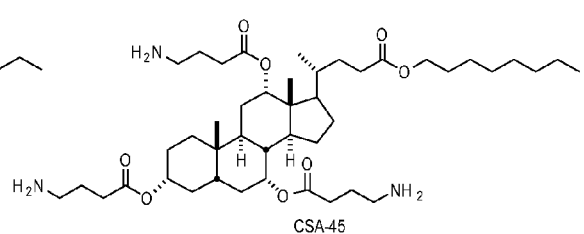
Figure 1:
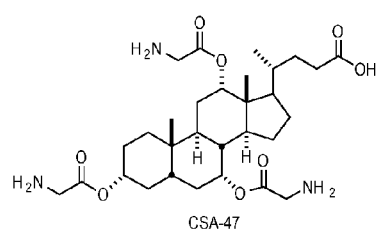
Figure 1:
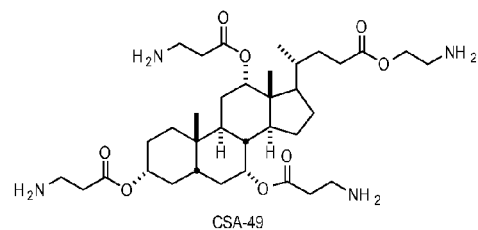
Figure 1:
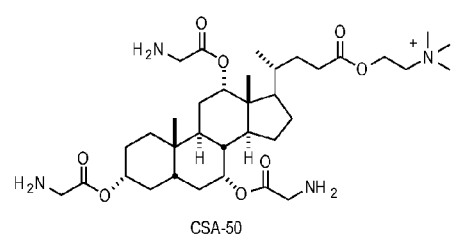
Figure 1:
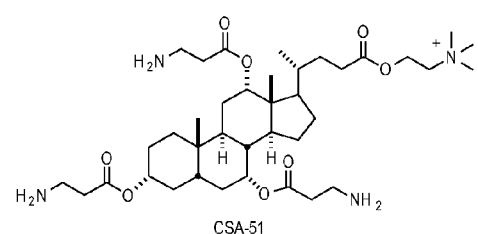
Figure 1:
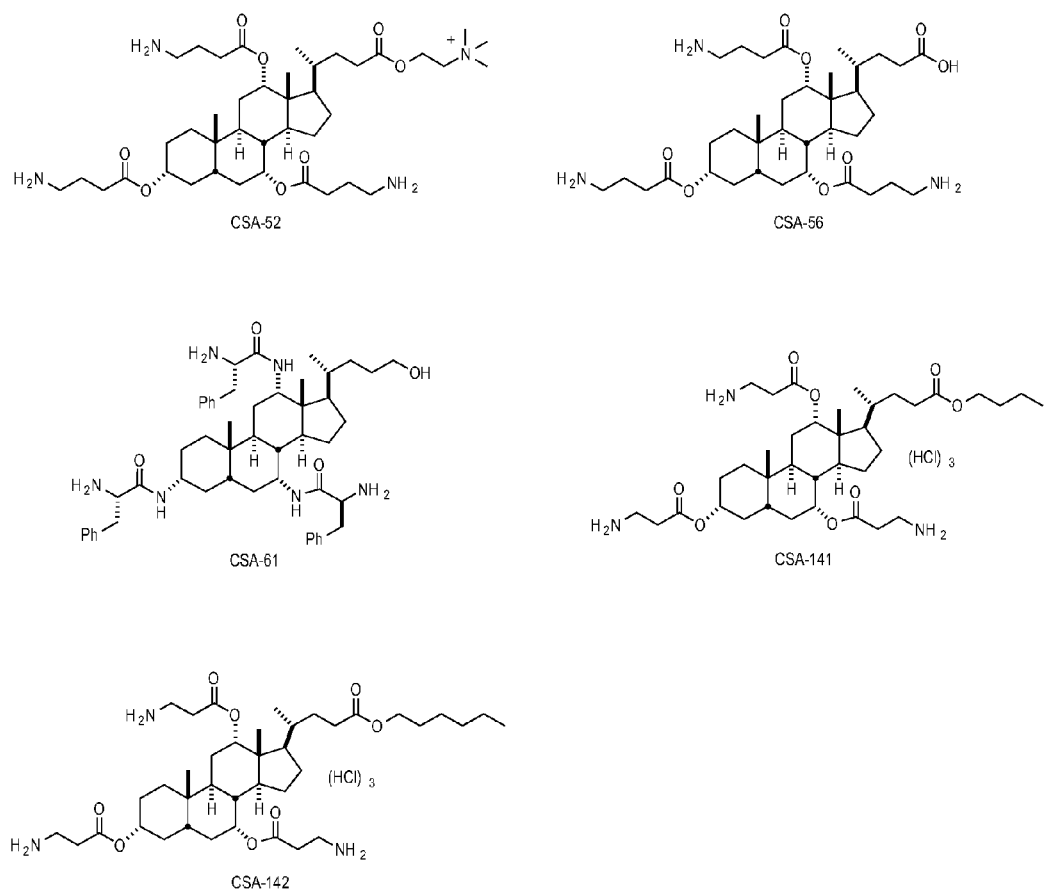

The charged groups are responsible for disrupting the bacterial cellular membrane, and without the charged groups, the ceragenin compound cannot disrupt the membrane to cause cell death or sensitization. Based on Scheme I and the above description, one can therefore appreciate that ceragenins having hydrolysable bonds linking the amino groups or similar charged groups to the sterol backbone can be inactivated by hydrolysis of the hydrolysable linkages and loss of the charged groups. A number of examples of ceragenin compounds having hydrolysable linkages are illustrated in FIG. 1.

II. Storage-Stable, Anti-Microbial Compositions

In one embodiment, a storage-stable, anti-microbial composition is described. The composition includes a carrier having a pH of 5.5 or less and a ceragenin compound suspended in the carrier. The ceragenin compound has a sterol backbone and a number of cationic groups attached thereto via hydrolysable linkages.

In one embodiment, the hydrolysable linkages are ester linkages. Such linkages are generally unstable in the presence of water and can be cleaved by water in a base catalyzed reaction. Thus, the linkages are stabilized at acidic pH. (e.g., a pH of 5.5 or less). An example of a ceragenin compound is shown below at Formula I. As will be discussed in greater detail below, the R groups on Formula I can have a variety of different functionalities, thus providing the ceragenin compound with different properties.

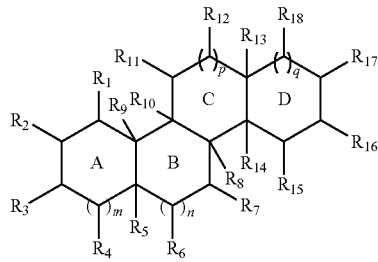

Formula I

The ceragenin compounds of the storage-stable, anti-microbial compositions described herein can be suspended in essentially any suitable carrier. In one embodiment, suitable carriers include, but are not limited to, water, alcohols, oils, petroleum jelly, organic solvents, organic/aqueous emulsions, and combinations thereof.

In one embodiment, the carrier includes water, an alcohol, and a surfactant. Suitable examples of surfactants include, but are not limited to, anionic surfactants (e.g., sodium lauryl sulfate and alkylbenzenesulfonates), cationic surfactants (e.g., CTAB), zwitterionic surfactants (e.g., CHAPS), and nonionic surfactants (e.g., Triton-X series detergents and polyethylene glycol monoalkyl ethers). The anti-microbial compositions described herein can also include one or more non-surfactant additives (e.g., EDTA, phosphonic acids, phosphinic acids, and the like). Such additives can, for example, enhance the wetting properties of the above described surfactants and/or chelate metals (e.g., copper, iron, magnesium, and the like), which may have mild anti-microbial effect.

In one embodiment, the carrier further includes an acid. In one embodiment, the acid is added to the carrier in an amount sufficient to reduce the pH of the carrier with the ceragenin compound suspended therein to a pH of about 5.5 or less. Suitable examples of acids that can be used to adjust the pH of the carrier include, but are not limited to, acetic acid, peracetic acid, citric acid, ascorbic acid, hydrochloric acid, sulfuric acid, nitric acid, and combinations thereof. In a specific embodiment, the acid is acetic acid added to the carrier with the ceragenin compound suspended therein at a concentration in a range from 0.01% to 1% (v/v) (e.g., about 0.5% (v/v)).

Figure 2:
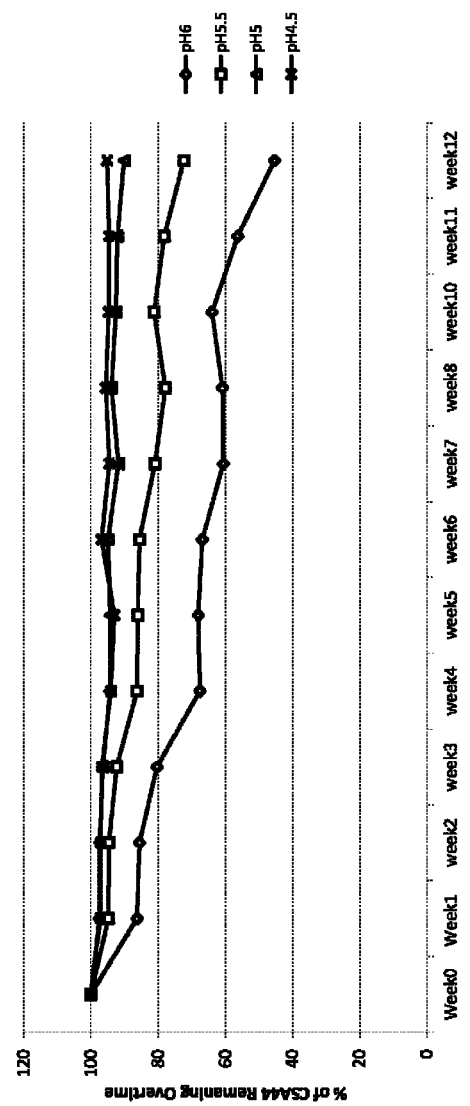
FIG. 2 is a graph illustrating the stability of CSA-44 as a function of pH.

Referring now to FIG. 2, a graph illustrating the stability of CSA-44 in aqueous solution over time as a function of pH is shown. CSA-44 includes ester-linked terminal amine groups attached at the $R_3$, $R_7$, and $R_{12}$ positions of Formula I. CSA-44 is illustrated in FIG. 1. As can be seen from FIG. 2, the stability of CSA-44 is greatly enhanced by lower pH. For example, at pH 6, only about 45% of the CSA-44 was still present after 12 weeks in aqueous solution. In contrast, at pH 5.5 over 72% was still present after 12 weeks. At pH 5 and 4.5 the stability was even better, with about 90%) and 95% remaining after 12 weeks, respectively.

TABLE 1

| CSA-44 Stability as a function of pH | | | | | | | |
|---|---|---|---|---|---|---|---|
| pH | Week 0 | Week 1 | Week 2 | Week 3 | Week 4 | Week 5 | Week 6 |
| 6 | 100 | 86.3 | 85.5 | 80.3 | 67.6 | 68.1 | 66.9 |
| 5.5 | 100 | 94.8 | 94.6 | 92.3 | 86.3 | 86.0 | 85.5 |

TABLE 1-continued

CSA-44 Stability as a function of pH

| | | | | | | |
|---|---|---|---|---|---|---|
| 5 | 100 | 97.5 | 97.4 | 96.4 | 94.3 | 94.2 | 94.9 |
| 4.5 | 100 | 97.2 | 97.0 | 96.7 | 94.1 | 93.0 | 96.8 |

| pH | Week 7 | Week 8 | Week 10 | Week 11 | Week 12 |
|---|---|---|---|---|---|
| 6 | 60.6 | 60.9 | 64.0 | 56.3 | 45.4 |
| 5.5 | 80.9 | 77.8 | 81.2 | 78.2 | 72.4 |
| 5 | 91.8 | 93.8 | 92.6 | 92.1 | 90.1 |
| 4.5 | 94.5 | 95.6 | 94.7 | 94.6 | 95.2 |

As such, in one embodiment, the carrier has a pH in a range of 2 to 5.5. In another embodiment, the carrier has a pH less than 5, 4.5, 4, 3.5, or 3 and greater than 1, 1.5, 2.0, or 2.5 or any range of the foregoing upper and lower pHs. At such acidic pHs, the ceragenin compound has a half-life of over 2 months, over 6 months, over 1 year, or over 2 years when suspended in the carrier.

In contrast, the ceragenin compounds are designed to break down relatively quickly if the pH environment of the ceragenin compounds is raised to about pH 6.5 or greater. One way that the pH environment of the ceragenin compounds can be changed is to apply the composition to a surface capable of raising the pH environment of the ceragenin compound to a pH greater than 6, 6.5, or 7. This can allow the ceragenin compounds described herein to effectively disinfect a wide variety of surfaces and substances without building up in the environment. In one embodiment, the ceragenin compound has a half-life of less than 1 day, less than 5 days, less than 10 days, less than 20 days, or less than 40 days when applied to a surface.

For example, the inventors in the present case have found that CSA-44 has a half-life of about 37 days at pH 7. However, the half-life of the ceragenin compounds described herein is likely to be shorter at higher pH. In addition, even though the ceragenin compounds described herein are not metabolized in the process of killing microbes, they are effectively inactivated when they are absorbed into the membrane of a microbe. As a result the effective half-life of the ceragenin compounds described herein (e.g., CSA-44) are likely to be substantially shorter in a microbe-contaminated environment than the half-life time needed for hydrolysis of the hydrolysable linkages.

In one embodiment, the carrier has a buffer concentration of less than 1 molar ("M"), 500 millimolar ("mM"), 100 mM, 75 mM, 50 mM, 25 mM, 10 mM, or 5 mM or less. In another embodiment, the carrier is substantially unbuffered. The buffering capacity of the carrier can affect the ability of a surface to raise the pH of the ceragenin compound after it is applied to the surface.

In one embodiment, the ceragenin compound may have a structure as shown in Formula I. In Formula I, at least two of $R_3$, $R_7$, or $R_{12}$ may independently include a cationic moiety attached to the Formula I structure via a hydrolysable linkage. Optionally, a tail moiety may be attached to Formula I at $R_{17}$. The tail moiety may be charged, uncharged, polar, non-polar, hydrophobic, amphipathic, and the like.

Suitable examples of ceragenin compounds of Formula I that have hydrolysable linkages include, but are not limited to, CSA-27, CSA-28, CSA-29, CSA-30, CSA-31, CSA-36, CSA-37, CSA-61, CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, CSA-142, or combinations thereof (see FIG. 1). Preferably, the ceragenin compound of Formula I includes one or more of CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, or CSA-142, or more preferably, the ceragenin compound of Formula I is CSA-44.

As discussed in greater detail above, the anti-microbial activity of the ceragenin compounds can be affected by the orientation of the substituents attached to the backbone structure. In one embodiment, the substituents attached to the backbone structure are oriented on a single face of the ceragenin compound. Accordingly, each of $R_3$, $R_7$, and $R_{12}$ are positioned on a single face of Formula I. In addition, $R_{17}$ may be positioned on the single face of Formula I.

III. Ceragenin-Containing Products

Suitable examples of products that may include the storage-stable, anti-microbial compositions described herein may include, but are not limited to, cleaning products, disinfecting solutions, topical anti-bacterial ointments, sprayable compositions (e.g., disinfectant sprays), gels, organic/aqueous emulsions, and the like.

In one embodiment, an anti-microbial product includes a packaging container and a storage-stable, anti-microbial composition disposed in the packaging container. In one embodiment, the storage-stable, anti-microbial composition includes a carrier having a pH of 5.5 or less and a ceragenin compound suspended in the carrier. In one embodiment, the ceragenin compound has a sterol backbone and a number of cationic groups attached thereto via a hydrolysable linkage.

Figure 3:
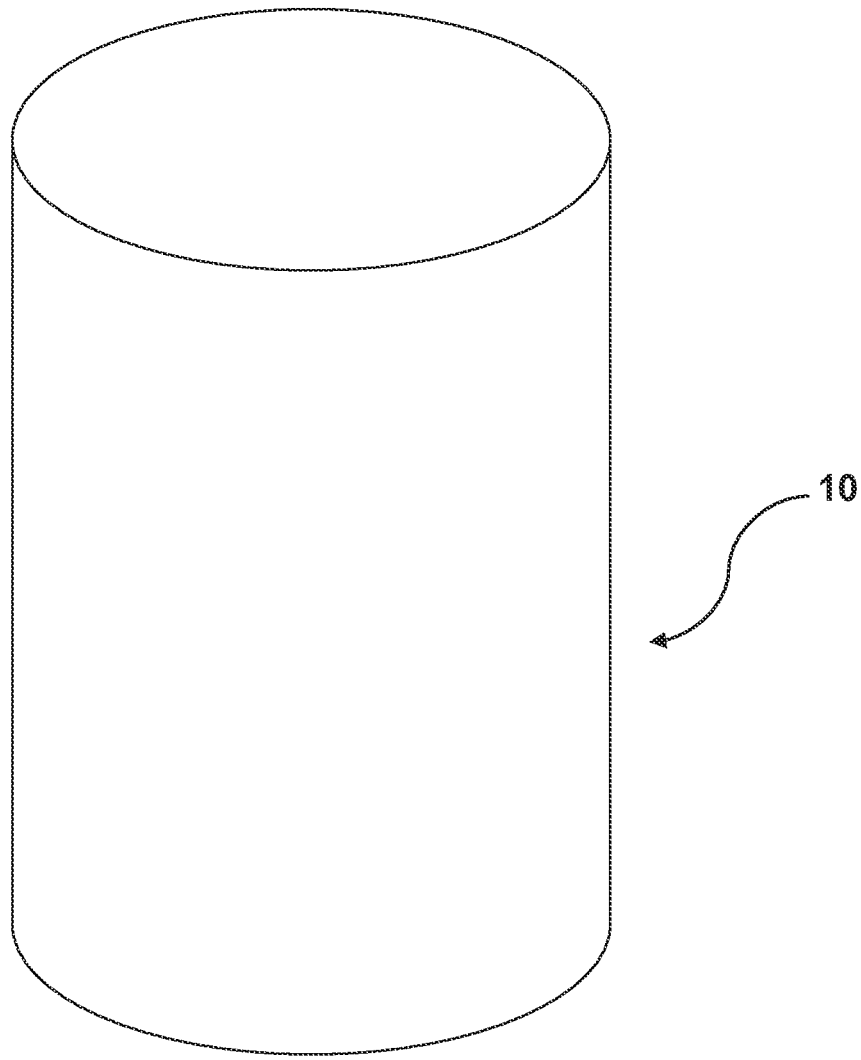
FIG. 3 schematically illustrates a packaging container, according to one embodiment of the present disclosure.

Referring now FIG. 3, a packaging container 10 is schematically illustrated. The packaging container 10 may be a bottle, a spray bottle, a jar, a tube, a carton, and the like.

A bottle is generally a rigid container with a neck that is narrower than the body and a "mouth" through which liquids can be dispensed. By contrast, a jar has a relatively large mouth or opening. Bottles are often made of glass, clay, plastic, aluminum or other impervious materials. Suitable examples of bottles may include any bottle used to store liquids.

A spray bottle is a bottle that can squirt, spray or mist fluids. In one embodiment, the stray bottle may be a trigger or pump spray bottle where a trigger or pump is depressed to dispense or mist fluid. In another embodiment, the spray bottle may be a spray can where the liquid in the bottle is stored under pressure and fluid is dispensed by pressing a trigger or the like.

The sprayable anti-microbial composition includes a liquid carrier having a pH of 5.5 or less and a ceragenin compound suspended in the liquid carrier. The ceragenin compound included in the sprayable anti-microbial composition has a sterol backbone and a number of cationic groups attached thereto via hydrolysable linkages.

In a specific embodiment of the sprayable anti-microbial composition, the liquid carrier includes water, at least one surfactant, and at least one alcohol, and the ceragenin compound is added to the sprayable anti-microbial composition in an amount in a range from about 0.01 weight % ("wt %") to about 0.4 wt % (e.g., about 0.02 wt %). The ceragenin compound included in this specific embodiment is at least one of CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, or CSA-142 (see FIG. 1).

In one embodiment, the storage-stable, anti-microbial composition includes a sprayable composition. In one embodiment, the liquid carrier of the sprayable composition includes water, an alcohol, a surfactant, and an acid.

In a specific embodiment of the present disclosure, the anti-microbial composition includes water, at least one surfactant, at least one alcohol, and at least one acid, and the ceragenin compound is added to the sprayable anti-microbial composition in an amount in a range from about 0.01 weight % ("wt %") to about 0.4 wt % (e.g., about 0.02 wt % to about 0.04 wt %).

A tube is a soft squeezable container that can be used for packaging thick liquids such as topical ointments. A tube is typically a cylindrical, hollow piece with a round or oval profile, made of plastic, paperboard, or aluminum having a capped end from which the contents of the tube can be dispensed and a crimped end.

Cartons for packaging liquids and the like can be fabricated from laminates of liquid packaging board, foil, and/or polyethylene. Examples include so-called "gable top" cartons that are typically used to package milk, juice, and the like and aceptic cartons that are used to package perishable liquids.

Suitable volumes for the packaging container include, but are not limited to, at least 10 ml, at least 15 ml, at least 20 ml, at least 50 ml, at least 75 ml, at least 100 ml, at least 200 ml, at least 250 ml, at least 500 ml, at least 750 ml, at least 1000 ml, or at least 1500 ml.

In one embodiment, the packaging container is a spray bottle and the storage-stable, anti-microbial composition is a disinfectant spray. Such sprays may be water based, alcohol based, or the like. Such sprays may include surfactants and other similar additives or they may be free of such additives.

In another embodiment, the packaging container is a tube and the storage-stable, anti-microbial composition is an anti-microbial ointment. Such ointment compositions are known in the art. Suitable examples of such ointments may include petroleum jelly based ointments, emulsions based ointments, gel based ointments, and the like.

IV. Methods for Disinfecting a Surface

In one embodiment, a method for disinfecting a surface is described. The method includes (1) applying an anti-microbial composition to a surface exposed to one or more microbes and (2) killing the one or more microbes on the surface. As in previously described embodiments, the ceragenin compound has a sterol backbone and a number of cationic groups attached thereto via hydrolysable linkages. In one embodiment, the hydrolysable linkages of the ceragenin compound are stabilized by lowering the pH of the carrier below a pH of about 5.5.

In one embodiment, the method further includes allowing the hydrolysable linkages to be hydrolyzed over a period of time after applying the anti-microbial composition to the surface, wherein the ceragenin compound has a half-life of less than 1 day, less than 5 days, less than 10 days, less than 20 days, or less than 40 days after being exposed to an environment capable of raising the pH of the ceragenin compound to a pH greater than 6, 6.5, or 7. In one embodiment, the environment capable of raising the pH of the ceragenin compound includes at least one of a bathroom surface, a kitchen surface, a food preparation surface, a food packaging surface, a hospital surface, a laboratory surface, or a waste water disposal surface (e.g., a sink or a water drain).

In one embodiment, the ceragenin compound in the anti-microbial composition is capable of continuing to kill microbes on the surface for at least one day after the applying, at least 5 days after the applying, or at least 10 days after the applying.

According to the present disclosure, the surface exposed to one or more microbes can be essentially any surface that is either known to be or suspected to be contaminated by or suspected to be exposed to one or more microbes. Suitable examples of microbes that may contaminate the surface include, but are not limited to, bacteria, fungi, and viruses. Suitable examples of surfaces include, but are not limited to, metallic surfaces, ceramic surfaces, wooden surfaces, polymer surfaces, biological surfaces, and combinations thereof. For example, the surface may include a food preparation surface, a food packaging surface (i.e., a surface that food is placed on for packaging and/or a surface inside a food packaging container), a bathroom surface, a hospital surface, a laboratory surface, a meat surface, a poultry surface, a fish surface, or a vegetable surface.

In one embodiment, at least one of the metallic surface, the ceramic surface, the wooden surface, the glass surface, or the polymer surface includes a food preparation surface or a food preparation area. For example, the food preparation surface may be a counter top, a cutting board, or a utensil. Food preparation areas can include floors, walls, sinks and the like.

In another embodiment, at least one of the metallic surface, the ceramic surface, the wooden surface, the glass surface, or the polymer surface includes a bathroom surface. For example, bathroom surfaces can includes, sinks, showers, tubs, toilets, floors, walls, and the like.

In another embodiment, at least one of the metallic surface, the ceramic surface, the wooden surface, the glass surface, or the polymer surface may include a food packaging surface. Food packaging surfaces may include surfaces that foods are positioned on in preparation for packaging or they may be one or more surfaces of a food package itself. For example, bacteria and mold growth inside food packages can lead to the spoilage of a wide variety of foods. Such microbial growth can conceivably be prevented or forestalled by treating food packaging surfaces with the anti-microbial compositions described herein.

In yet another embodiment, the biological surface includes at least one of a meat surface, a poultry surface, a fish surface, or a vegetable surface. Surprising and unexpectedly, the inventors in the present case have found that the ceragenin compounds described herein can be applied to a variety of fresh foods to kill bacteria and the like on the food and thereby prevent or forestall spoilage and/or prevent transmission of food borne illness. At the concentrations needed for food application, the ceragenin compounds described herein are tasteless, odorless, and they are safe for human consumption. In addition, the ceragenin compounds and certain compositions described herein can be applied to foods without discoloring or otherwise adversely affecting the quality of the food.

V. Ceragenin Compounds

The ceragenin compound may have a structure as shown in Formula I:

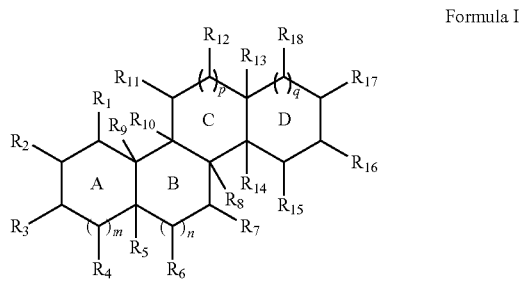

Formula I where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and ($C_1$-$C_{10}$) guanidinoalkylcarboxy, where $Q_5$ is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino($C_1$-$C_{10}$) alkyl, a substituted or unsubstituted ($C_1$-$C_{10}$) aminoalkyloxy-($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_5$) aminoalkylcarboxyamido, a ($C_1$-$C_{10}$) quaternaryammonium alkylcarboxy, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and a ($C_1$-$C_{10}$) guanidinoalkylcarboxy; or a pharmaceutically acceptable salt thereof.

In Formula I, at least two or three of $R_3$, $R_7$, or $R_{12}$ may independently include a cationic moiety attached to the Formula I structure via a hydrolysable linkage. Optionally, a tail moiety may be attached to Formula I at $R_{17}$. The tail moiety may be charged, uncharged, polar, non-polar, hydrophobic, amphipathic, and the like.

Although not required, at least two or three of m, n, p. and q are 1. In a preferred embodiment, m, n, and p=1 and q=0.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —$CH_2$—(C=O)—$NH_2$ (asparagine), —$CH_2$—SH (cysteine), and —CH(OH)—$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, CI, Br, and I), hydroxyl, protected hydroxyl, amino, protected amino, carboxy, protected carboxy, cyano, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, CI, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_6$-$C_{14}$, $C_{6-10}$ aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is ($C_1$-$C_{10}$) alkyloxy-($C_1$-$C_{10}$) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, *Protective Groups in Organic Chemistry*, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all β-substituted or α-substituted. The configuration of the moieties $R_3$, $R_7$ and $R_{12}$ may be important for interaction with the cellular membrane.

Compounds include but are not limited to compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from anyone, or more, of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula I. A tail moiety may include the heteroatom (O or N) covalently coupled to the sterol backbone.

The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A storage-stable, anti-microbial composition, comprising:
    a carrier having a pH greater than 2.0 and up to 5.5; and
    a ceragenin compound suspended in the carrier, the ceragenin compound having a sterol backbone and a number of cationic groups attached thereto via hydrolysable linkages, wherein the ceragenin compound has a half-life of over 2 months when suspended in the carrier.

2. The storage-stable, anti-microbial composition of claim 1, wherein the ceragenin compound has a half-life of less than 40 days when applied to a surface that raises the pH of the ceragenin compound to a pH of 7 or greater.

3. The storage-stable, anti-microbial composition of claim 1, wherein the carrier has a buffer concentration of 1 molar ("M") or less.

4. The storage-stable, anti-microbial composition of claim 1, wherein the carrier is selected from the group consisting of water, alcohols, oils, petroleum jelly, organic solvents, organic/aqueous emulsions, and combinations thereof.

5. The storage-stable, anti-microbial composition of claim 1, wherein the carrier includes a surfactant selected from the group consisting anionic surfactants, cationic surfactants, zwitterionic surfactants, and nonionic surfactants.

6. The storage-stable, anti-microbial composition of claim 1, the carrier comprising an acid selected from the group consisting of acetic acid, peracetic acid, citric acid, ascorbic acid, hydrochloric acid, sulfuric acid, nitric acid, and combinations thereof, wherein the acid is included in the carrier in an amount sufficient to reduce the pH of the carrier with the ceragenin compound suspended therein to a pH of greater than 2.0 and up to 5.0.

7. The storage-stable, anti-microbial composition of claim 1, wherein the hydrolysable linkage comprises an ester linkage.

8. The storage-stable, anti-microbial composition of claim 1, wherein the ceragenin compound is selected from the group consisting of CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, CSA-142, and combinations thereof.

9. The storage-stable, anti-microbial composition of claim 1, wherein:
    the carrier includes water, at least one surfactant, at least one alcohol, and at least one acid; and
    the ceragenin compound is added to the storage-stable, anti-microbial composition in an amount in a range from about 0.01 weight % ("wt %") to about 0.4 wt %, wherein the ceragenin compound is at least one of CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, or CSA-142.

10. An anti-microbial product, comprising:
    a packaging container; and
    a storage-stable, anti-microbial composition disposed in the packaging container, wherein the storage-stable, anti-microbial composition includes:
        a carrier having a pH of greater than 2.0 and up to 5.5; and
        a ceragenin compound suspended in the carrier, the ceragenin compound having a sterol backbone and a number of cationic groups attached thereto via a hydrolysable linkage, wherein the ceragenin compound has a half-life of over 2 months when suspended in the carrier.

11. The anti-microbial product of claim 10, wherein the packaging container is selected from the group consisting of bottles, spray bottles, jars, tubes, cartons, and combinations thereof.

12. The anti-microbial product of claim 10, wherein the packaging container is a spray bottle and the storage-stable, anti-microbial composition is a disinfectant spray.

13. The anti-microbial product of claim 10, wherein the packaging container is a tube and the storage-stable, anti-microbial composition is an antimicrobial ointment.

14. The anti-microbial product of claim 10, wherein the ceragenin compound has a half-life of less than 40 days when applied to a surface that raises the pH of the ceragenin compound to a pH of 7 or greater.

15. The storage-stable, anti-microbial composition of claim 1, wherein the carrier has a pH in a range of 2.5 to 5.5.

16. The storage-stable, anti-microbial composition of claim 1, wherein the ceragenin compound has a half-life of over 6 months when suspended in the carrier.

17. The storage-stable, anti-microbial composition of claim 1, wherein the ceragenin compound has a half-life of over 1 year when suspended in the carrier.

18. The storage-stable, anti-microbial composition of claim 1, wherein the ceragenin compound has a half-life of over 2 years when suspended in the carrier.

19. The storage-stable, anti-microbial composition of claim 1, wherein the ceragenin compound has a half-life of less than 20 days when applied to a surface that raises the pH of the ceragenin compound to a pH of 7 or greater.

20. The storage-stable, anti-microbial composition of claim 1, wherein the ceragenin compound has a half-life of less than 10 days when applied to a surface that raises the pH of the ceragenin compound to a pH of 7 or greater.

21. The storage-stable, anti-microbial composition of claim 1, wherein the ceragenin compound has a half-life of less than 5 days when applied to a surface that raises the pH of the ceragenin compound to a pH of 7 or greater.

22. A storage-stable, anti-microbial composition, comprising:
- a carrier comprising an acid selected from the group consisting of acetic acid, peracetic acid, citric acid, ascorbic acid, hydrochloric acid, sulfuric acid, nitric acid, and combinations thereof, wherein the acid is included in the carrier in an amount sufficient to reduce the pH of the carrier with the ceragenin compound suspended therein to a pH of greater than 2.0 and up to 5.5; and
- a ceragenin compound suspended in the carrier, the ceragenin compound having a sterol backbone and a number of cationic groups attached thereto via hydrolysable linkages, wherein the ceragenin compound has a half-life of over 2 months when suspended in the carrier.

* * * * *

UNITED STATES PATENT AND TRADEMARK OFFICE
CERTIFICATE OF CORRECTION

PATENT NO.        : 8,691,252 B2                                    Page 1 of 1
APPLICATION NO.   : 13/288892
DATED             : April 8, 2014
INVENTOR(S)       : Savage It is certified that error appears in the above-identified patent and that said Letters Patent is hereby corrected as shown below:

In the Specification

Column 1
Line 43, change "fresh food" to --fresh foods--

Column 3
Line 27, change "membrane forming" to --membrane, forming--
Line 62, change "acidic pH." to --acidic pH--

Column 4
Line 57, change "90%) and" to --90% and--

Column 5
Line 41, change "result the" to --result, the--

Column 6
Line 32, change "ajar" to --a jar--

Column 8
Line 20, change "includes" to --include--
Line 34, change "Surprising" to --Surprisingly--

Column 9
Line 64, change "n, p. and" to --n, p, and--

Column 10
Line 65, change "skill will" to --skill in the art will--

Signed and Sealed this
Twenty-second Day of July, 2014

Michelle K. Lee
*Deputy Director of the United States Patent and Trademark Office*